United States Patent
Wu Lee et al.

(10) Patent No.: US 11,013,720 B2
(45) Date of Patent: May 25, 2021

(54) GANETESPIB-CONTAINING PARTICLE, PHARMACEUTICAL COMPOSITION COMPRISING THE SAME, AND THEIR USE IN ANTICANCER TREATMENT

(71) Applicant: NATIONAL CHIAO TUNG UNIVERSITY, Hsinchu (TW)

(72) Inventors: Yan-Hwa Wu Lee, Taipei (TW); Dean-Mo Liu, Zhubei (TW); Wei-Ting Huang, Taitung (TW); Ru-Tsun Mai, New Taipei (TW); Yi-Hsin Chen, Nantou (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 16/520,553

(22) Filed: Jul. 24, 2019

(65) Prior Publication Data
US 2020/0368207 A1 Nov. 26, 2020

(30) Foreign Application Priority Data
May 24, 2019 (TW) .................. 108118072

(51) Int. Cl.
| | | |
|---|---|---|
| *A61K 31/4196* | (2006.01) |
| *A61K 47/36* | (2006.01) |
| *C07K 16/28* | (2006.01) |
| *A61P 35/00* | (2006.01) |
| *A61K 9/14* | (2006.01) |
| *A61K 31/517* | (2006.01) |
| *A61K 31/7068* | (2006.01) |
| *A61K 31/12* | (2006.01) |

(52) U.S. Cl.
CPC .......... *A61K 31/4196* (2013.01); *A61K 9/14* (2013.01); *A61K 47/36* (2013.01); *A61P 35/00* (2018.01); *C07K 16/2863* (2013.01); *A61K 31/12* (2013.01); *A61K 31/517* (2013.01); *A61K 31/7068* (2013.01)

(58) Field of Classification Search
CPC .. A61K 47/36; A61K 31/4196; A61K 31/517; A61K 31/7068; C07K 16/2863
See application file for complete search history.

(56) References Cited

U.S. PATENT DOCUMENTS

| | | | | |
|---|---|---|---|---|
| 8,263,130 B2* | 9/2012 | Chen | .................... | A61K 9/5161 424/489 |
| 9,345,718 B1 | 5/2016 | Weichert et al. | | |
| 2010/0098731 A1* | 4/2010 | Chen | .................... | A61K 9/5161 424/400 |
| 2014/0294808 A1* | 10/2014 | El-Hariry | .............. | C07D 403/04 424/133.1 |
| 2015/0342896 A1* | 12/2015 | Koyakutty | ........... | A61K 31/436 424/491 |
| 2015/0374672 A1 | 12/2015 | Vukovic et al. | | |
| 2016/0354315 A1 | 12/2016 | Li | | |
| 2017/0014519 A1 | 1/2017 | Chimmanamada et al. | | |
| 2017/0027877 A1* | 2/2017 | Huang | .................... | A61P 35/00 |
| 2017/0202970 A1 | 7/2017 | Foreman et al. | | |
| 2017/0368196 A1 | 12/2017 | Won et al. | | |
| 2018/0280517 A1* | 10/2018 | Huang | ................. | A61K 9/0019 |

FOREIGN PATENT DOCUMENTS

| | | |
|---|---|---|
| CN | 107249589 | 10/2017 |
| JP | 2014-34531 | 2/2014 |
| WO | 2016/183217 | 11/2016 |
| WO | 2017/147240 | 8/2017 |

OTHER PUBLICATIONS

Pucci et al (Ecancer Medical Science, 2019, vol. 13, p. 1-26) (Year: 2019).*
Jhaveri et al (Onco Targets and Therapy, 2015, vol. 8, pp. 1849-1858) (Year: 2015).*
Madrigal Pharmaceuticals (Synta announces Termination for Futility of Ganetespib Phase 3 GALAXY-2 Trial in Lung Cancer, Press Release, Oct. 2015) (Year: 2015).*
Choi et al., "Recent Updates on the Development of Ganetespib as a Hsp90 Inhibitor", Archives of Pharmacal Research vol. 35, No. 11, 2012, pp. 1855-1859.
Friedland et al., "Targeted inhibition of Hsp90 by ganetespib is effective across a broad spectrum of breast cancer subtypes", Invest New Drugs, vol. 32, 2014, pp. 14-24.
Jhaveri et al., "Ganetespib: research and clinical development", OncoTargets and Therapy, vol. 8, 2015, pp. 1849-1858.
Ono et al., "Enhanced antitumor activity of erlotinib in combination with the Hsp90 inhibitor CH5164840 against non-small-cell lung cancer", Cancer Science, vol. 104, No. 10, Oct. 2013, pp. 1346-1352.
Pillai et al., "Heat shock protein 90 inhibitors in non-small-cell lung cancer", Current Opinion in Oncology, vol. 26, No. 2, 2014, pp. 159-164.

(Continued)

*Primary Examiner* — Mark V Stevens
(74) *Attorney, Agent, or Firm* — Nixon & Vanderhye P.C.

(57) ABSTRACT

Disclosed herein is a ganetespib-containing particle, which includes an active ingredient selected from ganetespib, a pharmaceutically acceptable salt of ganetespib, and a combination thereof, and an amphiphilic chitosan-based carrier carrying the active ingredient. Also disclosed herein are a pharmaceutical composition including the ganetespib-containing particle, and use of such pharmaceutical composition in treating cancer.

14 Claims, No Drawings

(56) References Cited

OTHER PUBLICATIONS

Proia et al., "Ganetespib and HSP90: Translating Preclinical Hypotheses into Clinical Promise", Cancer Research, vol. 74, No. 5, Mar. 1, 2014, pp. 1294-1300.
Proia et al., "HSP90 inhibitor-SN-38 conjugate strategy for targeted delivery of topoisomerase I inhibitor to tumors", Molecular Cancer Therapeutics, vol. 14, 2015, pp. 1-11.
Shimamura et al., "Ganetespib (STA-9090), a Nongeldanamycin HSP90 Inhibitor, Has Potent Antitumor Activity in In Vitro and In Vivo Models of Non-Small Cell Lung Cancer" Clinical Cancer Research, vol. 18, No. 18, Sep. 15, 2012, pp. 4973-4985.
Smith et al., "The HSP90 inhibitor ganetespib potentiates the antitumor activity of EGFR tyrosine kinase inhibition in mutant and wild-type non-small cell lung cancer", Targeted Oncology, vol. 10, 2015, pp. 235-245.

\* cited by examiner

GANETESPIB-CONTAINING PARTICLE, PHARMACEUTICAL COMPOSITION COMPRISING THE SAME, AND THEIR USE IN ANTICANCER TREATMENT

CROSS-REFERENCE TO RELATED APPLICATION

This application claims priority of Taiwanese Patent Application No. 108118072, filed on May 24, 2019.

FIELD

The disclosure relates to a ganetespib-containing particle, in which ganetespib, a pharmaceutically acceptable salt of ganetespib, or a combination thereof is carried by amphiphilic chitosan, and a pharmaceutical composition comprising such particle. The disclosure also relates to use of the particle and the pharmaceutical composition in anticancer treatment.

BACKGROUND

Heat shock proteins are molecular chaperones that protect client proteins from degradation, in particular under conditions such as cellular stress, oxidative stress, and elevated temperature. Such proteins are frequently up-regulated in cancer and lead to cancer growth and metastasis. Heat shock protein 90 (HSP90) is a specific heat shock protein that plays an important role in protein folding and stabilizes many important oncogenic proteins in various types of cancer, such as epidermal growth factor receptor (EGFR), epidermal growth factor receptor 2 (HER2), anaplastic lymphoma kinase (ALK), protein kinase B (PKB), mitogen-activated protein kinase kinase (MEK), androgen receptor, estrogen receptor, etc.

Non-small cell lung cancer (NSCLC) is lethal lung cancer that accounts for about 85% of all lung cancer.

NSCLC is relatively insensitive to chemotherapy compared to small cell carcinoma. Surgical resection with curative intent, if feasible, is conducted to treat NSCLC. Nevertheless, since it has been shown that inhibition against HSP90 is promising in treating NSCLC, Hsp90 inhibitors have been developed to enhance the anticancer effect of therapy on NSCLC.

Ganetespib (4-[5-hydroxy-4-(1-methyl-1H-indol-5-yl)-4H-1,2,4-triazol-3-yl]-6-(propan-2-yl)benzene-1,3-diol), also referred to as STA-9090, is a resorcinol-based compound that binds to the ATP-binding pocket of HSP90 and hence leads to inhibition of HSP90. Due to its ability to inhibit HSP90, ganetespib can prevent client proteins from combining with HSP90, thereby giving rise to cell apoptosis. Therefore, ganetespib is considered effective against NSCLC.

However ganetespib might induce an undesired strong side effect (e.g. breathing difficulties, fatigue, fever, etc.), such that a high dosage of ganetespib should be avoided. Even though lipid-based and copolymer-based carriers have been used to encapsulate and deliver ganetespib, the drug encapsulation efficiency of such drug carriers is unsatisfactory, and the process of encapsulating ganetespib is complicated. Furthermore, the drug potency (which can be indicated by half maximal inhibitory concentration (IC50)) of ganetespib, when encapsulated by the aforesaid drug carriers, is also unsatisfactory.

The applicant has surprisingly found that amphiphilic chitosan, which is a linear polysaccharide containing β-(1, 4)-linked 2-amino-D-glucose (D-glucoseamine) and 2-acetamido-D-glucose (N-acetyl-D-glucose) units, can efficiently encapsulate ganetespib to form a particle effective in treating cancer. Particularly, the drug potency of ganetespib, when encapsulated by amphiphilic chitosan, can be improved compared to free ganetespib.

SUMMARY

Therefore, in a first aspect, the present disclosure provides a ganetespib-containing particle, which includes an active ingredient selected from the group consisting of ganetespib, a pharmaceutically acceptable salt of ganetespib, and a combination thereof, and an amphiphilic chitosan-based carrier carrying the active ingredient.

Ina second aspect, the present disclosure provides a pharmaceutical composition which includes the ganetespib-containing particle described above.

In addition, the present disclosure provides a method for treating cancer in a subject, which includes administering to the subject the pharmaceutical compoistion described above.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods andmaterials similar or equivalent to those described herein, which could be used in the practice of the present disclosure. Indeed, the present disclosure is in no way limited to the methods and materials described.

The applicant unexpectedly found in the examples below that ganetespib can be encapsulated by amphiphilic chitosan to form a particle which has drug potency higher than that of free ganetespib, and which can be prepared in an incomplicated manner.

Therefore, the present disclosure provides a ganetespib-containing particle, which includes an active ingredient selected from the group consisting of ganetespib, a pharmaceutically acceptable salt of ganetespib, and a combination thereof, and an amphiphilic chitosan-based carrier carrying the active ingredient.

In some embodiments, the active ingredient is ganetespib.

According to the present disclosure, the amphiphilic chitosan-based carrier have hydrophobic and hydrophilic moieties to respectively interact with hydrophobic and hydrophilic molecules. The amphiphilic chitosan-based carrier may include carboxymethyl-containing chitosan and/or derivatives thereof. Examples of carboxymethyl-containing chitosan and derivatives thereof include, but are not limited to, carboxymethyl-hexanoyl chitosan (CHC), CHC modified with (3-aminopropyl)triethoxysilane, oleoyl carboxymethyl chitosan (OCMC), N,N-dimethylhexadecyl carboxymethyl chitosan (DCMC), deoxycholic acid carboxymethyl chitosan (DACMC), N-octyl-O, N-carboxymethyl chitosan (OCC), OCC targeted with octreotide-Phe-polyethylene glycol-stearic acid, N-lauryl carboxymethyl chitosan, linoleyl carboxymethyl chitosan, linoleic acid poly(1,3-malic acid)

chitosan, cholesterol-modified O-carboxymethyl chitosan, N-cholesterol succinyl O-carboxymethyl chitosan, carboxymethyl chitosan-graft-phosphatidylethanolamine, folate-modified caroxymethyl chitosan, and cis-3-(9 H-purin-6-ylthio)-acrylic acid-graft-carboxymethyl chitosan. In an exemplary embodiment, the amphiphilic chitosan-based carrier is CHC.

According to the present disclosure, the ganetespib-containing particle may further include an additional active ingredient that is carried by the amphiphilic chitosan-based carrier. Examples of the additional active ingredient include, but are not limited to, gemcitabine (2'-deoxi-2',2'-difluorocytidine-monohydrochloride [betaisomere]), demethoxycurcumin (1,6-heptadiene-3,5-dione, 1-(4-hydroxy-3-methoxyphenyl)-7-(4-hydroxyphenyl), 17-allylam demethoxygeldanamycin (17-AAG), erlotinib (N-(3-Ethynylphenyl)-6,7-bis(2-methoxyethoxy)quinazolin-4-amine), retaspimycin, and a microRNA (miRNA) regulator.

According to the present disclosure, suitable miRNA regulators include, but are not limited to, miRNA upregulators (for instance, miRNA mimics) and miRNA downregulators (for instance, miRNA inhibitors). Suitable miRNA mimics include, but are not limited to, mimics for miRNA-183 family, mimics for miRNA-200 family, mimics for miRNA 34 family, mimics for miRNA-126 family, and mimics for miRNA-30-5-p family. Suitable miRNA inhibitors include, but are not limited to, inhibitors formiRNA-21 family and inhibitors formiRNA-155 family.

According to the present disclosure, the ganetespib-containing particle may further include a biologically functional molecule that is conjugated to one of the active ingredient and the amphiphilic chitosan-based carrier. Examples of the biologically functional molecule include, but are not limited to, anti-epidermal growth factor receptor (EGFR) antibodies, anti-epidermal growth factor receptor 2 (HER2) antibodies, anti-anaplastic lymphoma kinase (ALK) antibodies, anti-protein kinase B (PKB) antibodies, anti-mitogen-activated protein kinase kinase (MEK) antibodies, anti-androgen receptor antibodies, and anti-estrogen receptor antibodies. In some embodiments, the biologically functional molecule is an anti-EGFR antibody.

According to the present disclosure, the ganetespib-containing particle has a particle size that ranges from 30 nm to 500 nm. In some embodiments, the ganetespib-containing particle has a particle size that ranges from 50 nm to 200 nm. In other embodiments, the ganetespib-containing particle has a particle size that ranges from 50 nm to 100 nm.

Furthermore, the present disclosure provides a pharmaceutical composition which includes the ganetespib-containing particle described above.

In addition, the present disclosure provides a method for treating cancer in a subject, which includes administering to the subject the pharmaceutical compoistion described above.

According to the present disclosure, the cancer is selected from the group consisting of lung cancer, liver cancer, pancreatic cancer, breast cancer, colorectal cancer, and combinations thereof. In some embodiments, the cancer is lung cancer. In an exemplary embodiment, the cancer is non-small cell lung cancer.

The pharmaceutical composition according to the present disclosure can be formulated into a dosage form suitable for parenteral or oral administration using technology well known to those skilled in the art, which includes, but is not limited to, injections (e.g., sterile aqueous solutions or dispersions), sterile powder, tablets, troches, pills, capsules, and the like.

The pharmaceutical composition according to this disclosure can be parenterally administered via one or more of the following routes: intravenous injection, intramuscular injection, and subcutaneous injection.

In certain embodiments, the pharmaceutical composition is formulated into a dosage form suitable for oral administration.

The pharmaceutical composition according to this disclosure can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents,preservatives, lubricants, absorption delaying agents, plasticizer, filling agents, disintegrants, surfactants, thickening agents, liposomes, and the like.

The dosage and the frequency of administration of the pharmaceutical composition according to this disclosure may vary depending on the following factors: the severity of the disease to be treated, the route of administration, and the weight, age, physical condition and response of the subject to be treated. For instance, the daily dosage of the pharmaceutical composition according to this disclosure may be 50 mg to 150 mg per $m^2$ of body surface area, and may be administered in a single dose or in several doses.

The disclosure will be further described by way of the following examples. However, it should be understood that the following examples are solely intended for the purpose of illustration and should not be construed as limiting the disclosure in practice.

EXAMPLES

Experimental Materials:
1.Non-Small Cell Lung Carcinoma (NSCLC) Cell Lines

The following cell lines used in the examples were available from the Bioresource Collection and Research Center (BCRC) of the Food Industry Research and Development Institute (FIRDI) in Taiwan and/or the American Type Culture Collection (ATCC) in USA: human lung carcinoma cell line A549 (ATCC CCL-185; BCRC 60074) and human lung carcinoma cell line H1299 (ATCC CRL-5803).

The cells of the respective cell line were cultivated using a respective medium shown in Table 1 and a Petri dish in an incubator (37° C. and 5% $CO_2$). Medium change was performed approximately every two days. When about 80-90% confluence was reached, medium removal was conducted, followed by washing the cells two times with phosphate buffer saline (PBS). Trypsin-EDTA was added so as to detach the cells from the bottom of the Petri dish. Subsequently, a fresh medium was added to neutralize the activity of the trypsin, and the cells were sufficiently dispersed by virtue of repeated aspiration with a pipette. The resultant cell suspension was transferred to a flask, followed by cultivation in an incubator.

TABLE 1

| NSCLC Cell line | Medium |
| --- | --- |
| A549 | Dulbecco's Modified Eagle Medium (DMEM) supplemented with 10% fetal bovine serum (FBS) |
| H1299 | RPMI 1640 medium supplementedwith 10% FBS |

Example 1

Analysis of Ganetespib-Containing Particle According to Present Disclosure

To investigate the characteristics of the ganetespib-containing particle according to present disclosure and to verify whether such particle can carry a biologically functional molecule for enhancing the anti-cancer effect, the following experiments were conducted.

A. Preparation of Ganetespib-Containing Particle According to Present Disclosure 10 mg of ganetespib powder (purchased from Selleckchem) was dissolved in 0.5 mL of a dimethyl sulfoxide (DMSO) solution to prepare a ganetespib stock solution having a ganetespib concentration of 20 mg/mL. 5 uL of the ganetespib stock solution was added to 95 uL of a DMSO solution to obtain a diluted ganetespib solution having a ganetespib concentration of 1 mg/mL.

0.5 mg of carboxymethyl hexanoyl chitosan (CHC) (i.e. amphiphilic chitosan) powder (purchased from Advanced Delivery Technologies, Inc.) was added into an Eppendorf tube, followed by adding 50 uL of the diluted ganetespib solution. 0.95 mL of a 1× PBS solution was added into the resulting mixture so as to form 1 mL of a mixture solution (pH 7.4) having an initial CHC concentration of 0.5 mg/mL and an initial free ganetespib concentration of 50 μg/mL. The aforesaid procedure was repeated once to form another mixture solution having the same initial CHC concentration and the same initial free ganetespib concentration. Subsequently, the two mixture solutions were subjected to stirring at 4° C. for 12 hours and 24 hours, respectively, so that two CHC-ganetespib particle solutions (i.e. ganetespib-containing particle solutions) were formed.

B. Determination of Drug Encapsulation Efficiency of Ganetespib-Containing Particle Solutions The CHC-ganetespib particle solutions obtained in section A of this example were subjected to determination of drug encapsulation efficiency as follows.

The ganetespib stock solution was subjected to serial dilution to obtain standard ganetespib solutions respectively having the following free ganetespib concentrations: $10^5$ng/mL, $10^4$ng/mL, $10^3$ng/mL, 500 ng/mL, 250 ng/mL, and 125 ng/mL. The standard ganetespib solutions were subjected to determination of absorbance at 275 nm ($OD_{275}$) using a circular dichroism (CD) spectrophotometer (Model J-1700, Jasco). A standard curve was constructed based on the concentrations and $OD_{275}$ of the standard ganetespib solutions.

Furthermore, each of the CHC-ganetespib particle solutions was subjected to centrifugation at 10,000 rpm and 4° C. for 10 minutes. 500 uL of the resulting supernatant was obtained and was added into 500 uL of a methanol solution so as to form 1 mL of a test solution. Afterward, the test solution was subjected to determination of $OD_{275}$ using the CD spectrophotometer. The $OD_{275}$ of the test solution was compared to the standard curve so as to determine the unencapsulated ganetespib concentration (i.e. the remaining free ganetespib concentration). The drug encapsulation efficiency of the test solution was calculatd using the following equation (1):

$$A=[(B-C)/B]\times 100 \quad (1)$$

A=drug encapsulation efficiency (%)
B=initial free ganetespib concentration (50 ug/mL)
C=unencapsulated ganetespib concentration of respective test solution Results:

The experimental data obtained are expressed as mean±SD (standard deviation) or mean.

The CHC-ganetespib particle solutions prepared by 12 hours and 24 hours of stirring respectively had drug encapsulation efficiency of 51.4%±0.61% and 60%±0.25%. In other words, the CHC-ganetespib particle solutions prepared by 12 hours and 24 hours of stirring respectively had CHC-ganetespib particle concentrations (i.e. encapsulated ganetespib concentrations) of approximately 25.7 μg/mL and 30 μg/mL.

C. Determination of Physical Properties of Ganetespib-Containing Particle According to Present Disclosure A suitable amount of CHC powder as used in section A of this example was dissolved in 1 mL of a deionized (DI) solution to form a CHC particle solution having a CHC concentration of 0.5 mg/mL.

The CHC-ganetespib particles in the CHC-ganetespi particle solution with drug encapsulation efficiency of 60% and a CHC-ganetespib particle concentration of 30 μg/mL, which was obtained in section A of this example, were subjected to conjugation of an anti-epidermal growth factor receptor (EGFR) antibody. Specifically, 1 μL of an anti-mouse EGFR antibody (1 mg/mL in double distilled water) was added to the CHC-ganetespib particle solution, followed by stirring at 4° C. for 1 hour. 0.05 mL of a EDC (1-ethyl-3-(3-dimethylaminopropyl)carbodiimide) solution (0.1%, w/v) was added to the resulting solution, followed by being left standing for over 4 hours. Therefore, an anti-EGFR antibody conjugated particle solution containing anti-EGFR CHC-ganetespib particles (i.e. anti-EGFR antibody conjugated CHC-ganetespib particles) was formed. The anti-EGFR antibody conjugated particle solution was subjected to dertmination of drug encapsulation efficiency generally according to the method described in section B of this example.

The hydrodynamic diameter of the CHC particles, the CHC-ganetespib particles, and the anti-EGFR CHC-ganetespib particles was measured in double distilled water by virtue of dynamic light scattering (DLS) on BI-200SM Goniometer (Brookhaven Inc., Holtsville, N.Y.).

The zeta potential of the CHC particles, the CHC-ganetespib particles, and the anti-EGFR CHC-ganetespib particles was measured in double distilled water on a laser Doppler anemometry system (Beckman Coulter Inc., USA) to investigate the surface potential of these particles.

In addition, the CHC-ganetespib particles and the anti-EGFR CHC-ganetespib particles were observed using Jeol 2100 Transmission Electron Microscope (Jeol Ltd., Japan) under 20,000 magnification, so as to determine the particle size of these particles, and so as to confirm encapsulation of ganetespib by CHC and conjugation of the anti-EGFR antibody.

Results:

The experimental data obtained are expressed as mean±SD or mean.

The antibody-conjugated particle solution had drug encapsulation efficiency of 43%. In other words, the antibody-conjugated particle solution aproximately had an anti-EGFR CHC-ganetespib particle concentration (i.e. an encapsulated ganetespib concentration) of 21.5 μ.

The hydrodynamic diameter and zeta potential of the CHC particles, the CHC-ganetespib particles, and the anti-EGFR CHC-ganetespib particles are shown in Table 2 below.

TABLE 2

| Particle | Hydrodynamic diameter (nm) | Zeta potential (mV) |
|---|---|---|
| CHC | 65.69 ± 7.31 | 45 ± 0.33 |
| CHC-ganetespib | 158.29 ± 20.20 | 50.31 ± 0.43 |
| anti-EGFR CHC-ganetespib | 207.71 ± 27.97 | 40.17 ± 1.43 |

As shown in Table 2, the hydrodynamic diameter of the CHC-ganetespib particles was larger than that of the CHC particles, indicating that the drug ganetespib was successfully encapsulated by the drug carrier CHC to form a particle. Furthermore, the hydrodynamic diameter of the anti-EGFR CHC-ganetespib particles was larger than that of the CHC-ganetespib particles, indicating that the anti-EGFR antibody was successfully conjugated to the particle having ganetespib encapsulated by CHC.

Moreover, it could be verified by the zeta potential that the CHC-ganetespib particles and the anti-EGFR CHC-ganetespib particles, which had CHC encapsulating ganetespib, carried positive surface electric charges and hence were stable in an aqueous solution.

Turning to the observation by transmission electron microscopy, the particle size (about 200 nm) of the anti-EGFR CHC-ganetespib particles was larger than the particle size (about 50 to 100 nm) of the CHC-ganetespib particles, indicating that the anti-EGFR antibody was successfully conjugated to the particle having ganetespib encapsulated by CHC. In addition, it was shown by transmission electron microscopy that the drug ganetespib was successfully encapsulated by the drug carrier CHC to form a particle, and that the anti-EGFR antibody formed a shell structure on the particle having ganetespib encapsulated by CHC through conjugation (data not shown).

In view of the foregoing, amphiphilic chitosan can encapsulate ganetespib to form a particle, to which a biologically functional molecule can be further conjugated.

Example 2

Evaluation of Anticancer Effect of Ganetespib-Containing Particle According to Present Disclosure The anticancer effect of the ganetespib-containing particle according to present disclosure against NSCLC cells was evaluated in the following experiments, so as to investigate whether amphiphilic chitosan serving as a drug carrier can enhance the anticancer effect of ganetespib.

A. Preparation of Test Solutions Composed of Free Ganetespib or Ganetespib-Containing Particles The ganetespib stock solution obtained in section A of Example 1 was subjected to serial dilution to obtain free ganetespib test solutions respectively having the following free ganetespib concentrations: 25 ng/mL, 20 ng/mL, 12.5 ng/mL, 6.25 ng/mL, 3.125 ng/mL, and 1.5625 ng/mL. Moreover, the CHC-ganetespib particle solution with drug encapsulation efficiency of 60% and a CHC-ganetespib particle concentration of 30 μg/mL, which was obtained in section A of this example, was subjected to serial dilution to obtain CHC-ganetespib test solutions respectively having the following CHC-ganetespib particle concentrations: 20 ng/mL, 10 ng/mL, 5 ng/mL, 2.5 ng/mL, 1.25 ng/mL, and 0.625 ng/mL.

B. Determination of In Vitro Anticancer Effect Against A549 Cell Line

The A549 cells described in section 1 of Experimental Materials were placed in a 24-well culture plate at $1 \times 10^4$ cells/well, followed by cultivation in DMEM supplemented with 10% FBS at 37° C. and 5% $CO_2$. The A549 cells in the wells were respectively treated with the free ganetespib test solutions and the CHC-ganetespib test solutions. Specifically, 200 μL of a respective test solution was added into a corresponding well containing the A549 cells. The A549 cells which were not treated with the free ganetespib test solutions and the CHC-ganetespib test solutions served as a normal control. After the treatment, cultivation was conducted for 48 hours at 37° C. and 5% $CO_2$.

The respective resulting culture was subjected to washing twice with PBS after removal of the liquid in the well, and was subjected to determination of cell viability by virtue of the 3-(4,5-dimethylthiazol-2-yl)-2,5-diphenyltetrazoli-um-bromide (MTT) assay. Specifically, a suitable amount of a MTT solution (having a MTT concentration of 1.9 mg/mL) was added to the respective culture, followed by incubation for 4 hours. The liquid in the well was removed, and dimethylsulfoxide (DMSO) was added into the well to dissolve formazan dye. Absorbance of the mixture in the well at 450 nm ($OD_{450}$) was measured using a microplate reader (Tecan Sunrise, Switzerland). The cell viability (%) was calculated by substituting the absorbance into the following equation (2):

$$D = (E/F) \times 100 \quad (2)$$

D=cell viability (%)
E=$OD_{450}$ of respective culture
F=$OD_{450}$ of normal control $IC_{50}$ (half maximal inhibitory concentration) of the free ganetespib and the CHC-ganetespib particle agasint A549 cell line was determined based on the free ganetespib concentrations and the CHC-ganetespib particle concentrations, respectively, as well as the cell viability resulting from such concentrations.

Results:

The cell viability resulting from the various free ganetespib concentrations and the various CHC-ganetespib particle concentrations, as well as the $IC_{50}$ determined therefrom, are shown in Table 3 below.

TABLE 3

| Free ganetespib test solutions | | CHC-ganetespib test solutions | |
|---|---|---|---|
| Concentrations (ng/mL) | Cell viability (%, A549) | Concentrations (ng/mL) | Cell viability (%, A549) |
| 1.5625 | 98 | 0.625 | 90 |
| 3.125 | 70 | 1.25 | 72 |
| 6.25 | 52 | 2.5 | 48 |
| 12.5 | 40 | 5 | 40 |
| 25 | 30 | 10 | 25 |
| $IC_{50}$ (ng/mL) = 8.8 | | $IC_{50}$ (ng/mL) = 1.95 | |

As shown in Table 3, the $IC_{50}$ of the CHC-ganetespib particle agasint A549 cell line was approximately 4.5 times lower than that of the free ganetespib, manifesting that the anticancer effect of ganetespib against NSCLC cells can be significantly increased when ganetespib is encapsulated by amphiphilic chitosan. In addition, the much lower $IC_{50}$ of the CHC-ganetespib particles indicates that the drug dosage required for effectively treating NSCLC cells can be greatly lowered when ganetespib is encapsulated by amphiphilic chitosan, greatly reducing the side effect of ganetespib.

C. Determination of In Vitro Anticancer Effect Against H1299 Cell Line

The in vitro anticancer effect of the free ganetespib and the CHC-ganetespib particle agasint H1299 cell line was determined generally according to the method described in section B of this example, except that the H1299 cells described in section 1 of Experimental Materials were placed in a 24-well culture plate at $5\times10^4$ cells/well, followed by cultivation in RPMI medium supplemented with 10% FBS.

Results:

The cell viability resulting from the various free ganetespib concentrations and the various CHC-ganetespib particle concentrations, as well as the $IC_{50}$ determined therefrom, are shown in Table 4 below.

TABLE 4

| Free ganetespib test solutions | | CHC-ganetespib test solutions | |
| --- | --- | --- | --- |
| Concentrations (ng/mL) | Cell viability (%, H1299) | Concentrations (ng/mL) | Cell viability (%, H1299) |
| 1.5625 | 93 | 1.25 | 80 |
| 3.125 | 85 | 2.5 | 68 |
| 6.25 | 55 | 5 | 52 |
| 10 | 48 | 10 | 30 |
| 20 | 23 | 20 | 12 |
| IC50 (ng/mL) = 10.3 | | IC50 (ng/mL) = 4.3 | |

As shown in Table 4, the $IC_{50}$ of the CHC-ganetespib particle agasint H1299 cell line was approximately 2.5 times lower than that of the free ganetespib, manifesting that the anticancer effect of ganetespib against NSCLC cells can be significantly increased when ganetespib is encapsulated by amphiphilic chitosan. In addition, the much lower $IC_{50}$ of the CHC-ganetespib particle indicates that the drug dosage required for effectivly treating NSCLC cells can be greatly lowered when ganetespib is encapsulated by amphiphilic chitosan, greatly reducing the side effect of ganetespib.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A ganetespib-containing particle comprising:
    an active ingredient selected from the group consisting of ganetespib, a pharmaceutically acceptable salt of ganetespib, and combinations thereof; and
    an amphiphilic chitosan-based carrier carrying the active ingredient, wherein the amphiphilic chitosan-based carrier is carboxymethyl-hexanoyl chitosan (CHC).

2. The ganetespib-containing particle as claimed in claim 1, further comprising an additional active ingredient carried by the amphiphilic chitosan-based carrier.

3. The ganetespib-containing particle as claimed in claim 2, wherein the additional active ingredient is selected from the group consisting of gemcitabine, demethoxycurcumin, 17-allylam demethoxygeldanamycin, erlotinib, retaspimycin, a microRNA regulator, and combinations thereof.

4. The ganetespib-containing particle as claimed in claim 1, further comprising a biologically functional molecule conjugated to the active ingredient or the amphiphilic chitosan-based carrier.

5. The ganetespib-containing particle as claimed in claim 4, wherein the biologically functional molecule is selected from the group consisting of an anti-epidermal growth factor receptor (EGFR) antibody, an anti-epidermal growth factor receptor 2 antibody, an anti-anaplastic lymphoma kinase antibody, an anti-protein kinase B antibody, an anti-mitogen-activated protein kinase kinase antibody, an anti-androgen receptor antibody, an anti-estrogen receptor antibody, and combinations thereof.

6. The ganetespib-containing particle as claimed in claim 5, wherein the biologically functional molecule is an anti-EGFR antibody.

7. The ganetespib-containing particle as claimed in claim 1, which has a particle size ranging from 30 nm to 500 nm.

8. The ganetespib-containing particle as claimed in claim 7, which has a particle size ranging from 50 nm to 200 nm.

9. A pharmaceutical composition comprising a ganetespib-containing particle as claimed in claim 1.

10. The pharmaceutical composition as claimed in claim 9, further comprising an additional active ingredient carried by the amphiphilic chitosan-based carrier.

11. The pharmaceutical composition as claimed in claim 10, wherein the additional active ingredient is selected from the group consisting of gemcitabine, demethoxycurcumin, 17-allylam demethoxygeldanamycin, erlotinib, retaspimycin, a microRNA regulator, and combinations thereof.

12. The pharmaceutical composition as claimed in claim 9, further comprising a biologically functional molecule conjugated to the active ingredient or the amphiphilic chitosan-based carrier.

13. The pharmaceutical composition as claimed in claim 12, wherein the biologically functional molecule is an anti-epidermal growth factor receptor antibody.

14. A method for treating cancer in a subject, comprising:
    administering to the subject a pharmaceutical composition as claimed in claim 9,
    wherein the cancer is selected from the group consisting of non-small cell lung cancer, breast cancer, and combinations thereof.

* * * * *